United States Patent [19]
Cabral et al.
[11] Patent Number: 4,830,753
[45] Date of Patent: May 16, 1989

[54] MEMBRANE FILTRATION OF CELL CULTURE MEDIA WITH CHARGED PARTICLES

[75] Inventors: Joaquim M. S. Cabral, Lisboa, Portugal; Elizabeth M. Robinson, Cambridge; Charles L. Cooney, Brookline, both of Mass.

[73] Assignee: Rohm and Haas Company, Philadelphia, Pa.

[21] Appl. No.: 34,657

[22] Filed: Apr. 10, 1987

Related U.S. Application Data

[63] Continuation-in-part of Ser. No. 854,981, Apr. 28, 1986, abandoned.

[51] Int. Cl.$^4$ .......................... B01D 13/00; B01D 5/04

[52] U.S. Cl. .................................... 210/638; 210/650; 210/663

[58] Field of Search ......................... 210/638, 650–655, 210/685, 686, 692, 778, 663, 639

[56] References Cited

U.S. PATENT DOCUMENTS

| | | | |
|---|---|---|---|
| 4,007,115 | 2/1977 | Howe | 210/692 |
| 4,200,695 | 4/1980 | Chong et al. | 210/686 |
| 4,663,048 | 5/1987 | Tanaka et al. | 210/638 |

*Primary Examiner*—Ivars Cintins

[57] ABSTRACT

In the membrane filtration of a liquid cell culture medium, superior flux rates and product recovery are obtained when a first charged particulate material and optionally a second charged particulate material bearing a charge opposite that of the first material are sequentially added to the medium prior to filtration.

15 Claims, No Drawings

MEMBRANE FILTRATION OF CELL CULTURE MEDIA WITH CHARGED PARTICLES

This Application is a continuation-in-part of co-pending U.S. application, Ser. No. 854,981, filed Apr. 28, 1986 and since abandoned.

TECHNICAL FIELD

This invention relates to a method for filtering liquid cell cuture media, such as fermentation broths, using charged particles as filtering aids and, more particularly, to membrane filtration methods in which the charged particles are combinations of microsized positively and negatively charged particles.

BACKGROUND OF THE INVENTION

The use of charged particles as filtering aids in the membrane filtration of liquid cell culture media such as fermentation liquors is known. U.S. Pat. No. 4,200,659 to Chong et al describes flocs prepared by mixing microsized, positively and negatively charged particles and the use of these preformed flocs as filtering agents for fermentation broths, and suggests that negatively or positively charged particles individually may be ultrafiltered within the lumens of fine hollow fibers (col. 9, line 59 to col. 10, line 44). In another context (col. 12, lines 17-30), the Chong et al. patent describes preparation of the flocs in the liquid to be treated and filtered by adding negatively and positively charged particles to the liquid.

Combinations of fine-particle-size, positively and negatively charged polymeric adsorbents have also been used sequentially for other purposes, such as the removal of humic substances from potable water which react with chlorine to produce toxic trihalomethanes, as described in U.S. Pat. No. 4,537,683 to Isacoff and Neely, or simultaneous decolorization and clarification of impure sugar solutions, as described by Cartier, U.S. Pat. No. 4,247,340.

SUMMARY OF THE INVENTION

It has now been found, surprisingly, that if a first microsized, charged particulate material is mixed with a liquid cell culture medium, one obtains several highly significant advantages when the resulting suspensions are membrane filtered. These and other advantages may also be obtained or enhanced if the mixture is subsequently mixed with a second microsized, charged particulate material bearing a charge opposite that of the first charged particulate material.

Such as an advantage is a 20% to several-fold increase in flow rate through a filtration membrane, resulting at least partially from a substantial reduction in the formation of secondary layers of particles and/or solutes on the membrane surface (the concentration polarization phenomenon) which tend to gelatinize and to foul the membrane, and partially from a change in the membrane rejection coefficient. The commercial advantage of such an advantage is readily apparent.

In this specification, the expression "cell culture medium" means a fermentation broth, i.e., the liquid medium in which biological substances are grown, or filtrates or liquid fractions obtained from fermentation broths, including or excluding cells, cell debris and other material resulting from cell lysis, if practiced. The biological substances include plant, animal and microbial cells, genetically engineered cells, and products thereof.

DETAILED DESCRIPTION OF THE INVENTION

The preferred charged particulate materials useful in the method of the invention are fine particle size resins such as described in the previously mentioned patents: Chong et al., U.S. Pat. No. 4,200,695 and Isacoff et al., U.S. Pat. No. 4,537,683 which patents are incorporated herein by reference. Small charged particles of other types functionality and/or exchange capacities may be used, such as conventional resins produced by suspension polymerization or other technique, provided the resins have effective charge densities and particle size for use in the invention. The particle size of these resins may be reduced, as needed, by grinding in a known manner. Such resins are described, for example, in U.S. Pats. Nos. 3,037,052; 3,637,535; 3,843,566; 3,791,866; 3,275,548; and 3,357,158, all of which are incorporated herein by reference. Other charged particles useful in the present invention include, but are not limited to, those particles having a diameter of 2.5 micrometers or smaller, which are insoluble in the liquid medium in which they are to be used and which have a charge at their surfaces that is available for interaction with other components in the liquid medium.

The resins of the Chong et al. and Isacoff et al. patents, be they positively or negatively charged, are composed of crosslinked polymers in the shape of approximately spherical beads having diameters in the range of about 0.01-1.5 micrometers. Useful resins bear about 0.1-1.5 functional groups per monomer unit, which groups can be strongly acidic (e.g., $-SO_3H$ groups), weakly acidic (e.g., $-COOH$ groups), strongly basic (e.g., quaternary ammonium groups), or weakly basic (e.g., tertiary amine groups).

Fermentation broths which may be filtered according to the invention are produced by growing fungi, yeasts, bacteria or other cells of biological origin in conventional liquid culture media. After microbial growth and fermentation are finished, the broth will contain cells, cell debris, spent nutrients, biological products and various contaminants. The broths may themselves be filtered in accordance with the method of the invention or the solid material may first be removed by centrifugation, conventional filtration or other separation techniques and the invention practiced on the supernatant or any fraction thereof. The invention may also be practiced both on the fermentation broth and on any liquid portions or fractions thereof, including the supernatant.

The particular charged particles to be used in any given case is a matter of selection, based on well-known principles of microbiology and fermentation biochemistry in light of the charge and charge densities of solids and solutes in the cell culture media, and is easily made by one skilled in these arts. The terms "charged particle" and "charged particulate material" as used herein, are understood to include all particles bearing charges that are available for interaction with other components in a liquid medium, including charges limited to the particle surface; it includes both deliberately functionalized particles and those with naturally occurring charges, as well as particles both soluble and insoluble in the liquid medium.

The method of this invention is carried out by adding the first charged particulate material of choice to the cell culture medium and then stirring the mixture until the suspension is homogeneous. In a preferred embodiment, a second charged particulate material of choce, having a charge opposite that of the first material, is then added to the broth, with stirring. The floc which forms in the medium will contain the charged particles, microbial cells (if present) and other broth components including particulate components and charged components, if present.

In a more preferred embodiment of the method of this invention, the first charged particulate material is positively charged and immediately forms a floc with negatively charged components of the broth. The optional, subsequent addition of the negatively charged material stabilizes and increases the size of the previously formed floc by interacting with the positively charged material and other broth components.

The amount of each of the charged particles ordinarily is in the range of about 0.01–0.5% by volume of broth, preferably 0.1–0.25%.

The resulting suspension is then passed through a membrane filter in the usual manner. Typically, the membrane filters are those semipermeable membranes known in the art for their ability to remove dissolved or dispersed matter by ultrafiltration or microfiltration, but excluding separation of dissolved salts by a technique known as reverse osmosis.

In summary, the transmembrane flux rate of cell culture media is vastly improved by use of the combined, microsized, charged particles in accordance with the invention, the high flux rate remaining constant, in some cases, over at least a five-fold concentration of the medium. At the same time, when the invention is practiced on media containing proteins, enzymes and other products to be purified or recovered, there is decreased concentration polarization and reduced rejection of these products by the membrane filtration, which results in a more complete separation and improved recovery of the products. These benefits depend on formation of a floc upon addition of the first charged particulate material; additional benefits depend on stabilization of the floc by subsequent addition of the second charged particulate material. The stabilization is believed to result from the linking of complex cells (or other materials), positively charged particles, solutes and negatively charged particles through ionic interactions. It is believed that the floc adsorbs and removes from the liquid medium those components that are responsible for low flux rates in untreated media. Even in those cases in which the viscosity of the cell culture medium increases in the presence of the floc, the resultant decreases in flux rate are counteracted by decreases in formation of gel layers on the membrane caused by concentration polarization.

Those skilled in the art will be able to efficiently practice the invention after referring to the following illustrative examples. These artisans will be able to compose numerous variations on the themes disclosed, such as changing the amounts of ingredients slightly but insignificantly from those shown, adding innocuous substances, or substituting equivalent or nearly equivalent components for those shown. All these variations are considered to be part of the inventive concept. In these examples, all parts and percentages are by weight unless otherwise indicated.

The charged particulate materials of the examples are prepared by emulsion polymerization as described in U.S. Pats. Nos. 4,200,695 and 4,537,683 and are characterized as follows:

Resin A: Strong Base, quaternary amine functionalized, styrene-divinylbenzene-aminoalkyl methacrylate gellular copolymer, 5% crosslinker, having an anion exchange capacity=2.8 meq/g dry and average particle diameter=0.11±0.02 micrometer, chloride form.

Resin B: Strong acid, sulfonic acid functionalized, styrene-divinylbenzene gellular copolymer, 7.3% crosslinker, having a cation exchange capacity=5.1 meq/g dry and average particle diameter=0.26±0.02 micrometer, hydrogen form.

Resin C: Strong base, quaternary amine functionalized, styrene-divinylbenzene gellular copolymer, 1.8% crosslinker, having an anion exchange capacity of 3.8 meq/g dry and an average particle diameter of 0.22±0.02 micrometer.

Resin D: Strong base, quaternary amine functionalized, styrene-divinylbenzene macroreticular copolymer, 3% crosslinker, having an anion exchange capacity of 4.0 meq/g dry, ground to an average particle size of 1.1 micrometer and a range of smaller than 0.4 micrometers to 5 micrometers.

Examples 1 and 2 describe the effects on flux rate and protein recovery of treatment of a fermentation broth with Resin A and Resin B, respectively, for comparison with treatments of the combined resins (Example 3). Example 4 describes ultrafiltration of fermentation broths treated with the combined resins, and concentration by ultrafiltration of the separated, resuspended flocs. Example 5 shows flux rates and protein recovery when particle-free supernatants of the preparation of Example 4 are ultrafiltered with the combination of resins. Example 6 is similar to Example 5 but shows effects of the combined resin ultrafiltration on cell-free supernatants. Examples 7 and 8 show the effect on ultrafiltration and microfiltration flux rates, respectively, of a fermentation broth treated with Resin A. Example 9 shows the effect of other small anion exchange resins on microfiltration of a fermentation broth. Examples 10 and 11 show the effect of combined Resins A and B and on ultrafiltration and microfiltration of a yeast cell suspension, while Example 12 shows the effect of combined Resins A and B on microfiltration of an albumen sample.

EXAMPLE 1

Whole cells of *Bacillus licheniformis*, ATCC 21415, were grown on a liquid medium containing 3% starch, 1% glucose, 5% soybean meal hydrolysate, 1% ammonium phosphate, 0.03% potassium chloride and 0.02% magnesium sulfate at 30° C. and pH 7.0 for four days. The final dry cell weight was 10 g/liter. At the end of culivation, 1 liter of crude fermentation broth was concentration by ultrafiltration at room temperature through using a hollow fiber filtration module with porosity of 100,000 MW (Romicon HF-1-43 PM 100). The hollow fiber module consists of membranes made from polysulfone. This module has twenty-five fibers with an internal diameter of 1.1 mm, a surface area of 930 $cm^2$ and a length of 40 cm. The operating parameters used were a mean transmembrane pressure of 117 kPa and recirculation flow rate of 2 liters/min.

The average flux permeate rate was measured and compared with those obtained when a floc formed by the addition of Resin A was added to the fermentation broth. The initial extracellular protein, the protein adsorbed in the membrane and the protein rejection were also determined.

The average transmembrane filtrate flux rate in this and subsequent examples was calculated in a known manner, using Simpson's rule in the integration of the flux rate, $\bar{J}$, obtained over a filtration time corresponding to a 5- to 7-fold cell concentration:

$$\bar{J} = \frac{1}{t} \int_0^{t_c} J dt$$

where

J is the instantaneous flux rate, t is time, and $t_c$ is the time required to reach a specific concentration.

The results of the measurements are given in Table 1 from which it will be seen that improvement in flux rate was obtained over the control, the improvements increasing with Resin A concentration.

TABLE 1

Influence of microsized anion exchange resin on the ultrafiltration characteristics of a *B. licheniformis* broth.

| Resin A Concentration (%, wt/v) | Average Transmembrane Flux Rate (liter/hr/m²) |
|---|---|
| 0 | 12.5 |
| 0.05 | 19.6 |
| 0.10 | 26.9 |
| 0.25 | 31.5 |

EXAMPLE 2

The procedure of Example 1 was repeated in all essential respects except that Resin B was used in place of Resin A. No floc formed upon admixture of the broth with Resin B. The results are shown in Table 2 and indicate substantially lower efficiency than was achieved with Resin A in Example 1.

TABLE 2

Influence of microsized cation resin on the ultratiltration characteristics of a *B. licheniformis* broth.

| Resin B Concentration (%, wt/v) | Average Transmembrane Flux Rate (liter/hr/m²) |
|---|---|
| 0 | 12.5 |
| 0.05 | 17.0 |
| 0.10 | 19.0 |
| 0.25 | 21.9 |

EXAMPLE 3

The procedure of Example 1 was repeated in all essential respects except that the effect on the performance of the ultrafiltration of adding both Resin A and Resin B was studied. Table 3 shows the results as compared with the control (Table 1). It will be seen that when comparing treatments with resins of the same concentrations, a substantial increase in flux rate was obtained when the order of addition was reversed. Resin A followed by Resin B represents a 24.7% increase in flux rate over that of the run in which Resin B was followed by Resin A.

The protein effectively rejected by the membrane is defined as the total amount of protein present in the concentrate fraction plus the total protein in the concentration polarized gel layer associated with the membrane. The protein in the gel layer (ΔP) is obtained by difference between the total protein present in the cleared supernatant of the starting broth and the sum of the protein in the filtrate (permeate) and the cleared concentrate after filtration. Protein rejection in this and subsequent examples is expressed as the percentage of the starting protein in solution that was not recoverable in the filtrate; the calculation is:

$$\text{Average Protein Rejection} = 1 - \frac{\ln\left(1 - \frac{P_f V_f}{P_i V_i}\right)}{\ln\left(1 - \frac{V_f}{V_i}\right)}$$

where $P_f$=the protein, in milligrams, in the filtrate fraction $V_f$=the volume, in milliliters, of the filtrate fraction $P_i$=the initial protein in solution (mg)

$V_i$=the initial solution volume (ml)

TABLE 3

Influence of order of addition and amounts of Resins A and B on ultrafiltration characteristics of a *B. licheniformis* broth.

| Resin Added First | Resin Added Second | Flux (liter)/(hr × m²) | Protein Rejection | Enzyme Rejection |
|---|---|---|---|---|
| none | none | 12.5 | 0.91 | 0.18 |
| Resin B (0.10%) | Resin A (0.10%) | 20.3 | 0.89 | 0.08 |
| Resin B (0.10%) | Resin A (0.25%) | 29.5 | 0.89 | 0.41 |
| Resin B (0.25%) | Resin A (0.10%) | 29.8 | 0.88 | 0.14 |
| Resin A (0.25%) | Resin B (0.10%) | 36.9 | 0.76 | 0.09 |

EXAMPLE 4

(A). Cell cultivation was carried out for 48 hours essentially as described in Example 1. The resulting dry cell weight was 4 g/liter. To 1 liter of the fermentation broth were added Resin A and then Resin B to final 0.25% and 0.10% concentrations, respectively. The control sample was 1 liter of the fermentation broth.

(B). *B. lichenformis* cells and flocculated structures, containing mixed resins, whole cells and components of the medium, were separated by centrifugation at 7,000×g for 10 minutes from the control and the treated sample of (A) above. The particulate material, whole cells or flocs were washed with 1 liter of distilled water, centrifuged for 10 minutes and resuspended in distilled water at the same volume as the initial samples (1 liter). The water-suspended whole cells (control) and the water-suspended flocs were concentrated by ultrafiltration, using the same cartridge as described in Example 1. Average flux rates are shown in Table 4. It will be noted that the combination of Resins A and B greatly increased the flux rate.

TABLE 4

Influence of mixed ion exchange resin flocs on flux of *B. licheniformis* water suspensions

| Sample Treatment | Average Transmembrane Flux Rate (liter/hr/m²) |
|---|---|
| Control, no additions (washed cells) | 77 |

TABLE 4-continued

Influence of mixed ion exchange resin flocs on flux of *B. licheniformis* water suspensions

| Sample Treatment | Average Transmembrane Flux Rate (liter/hr/$m^2$) |
| --- | --- |
| Resin A (0.25%) + Resin B (0.1%) (washed flocs) | 104 |

EXAMPLE 5

The procedure of Example 4 was repeated in all essential respects except that the performances of the ultrafiltration of the supernatants of the preparations described in Example 4 were measured (Table 5). The substantial improvements afforded by the combined resins are readily apparent.

TABLE 5

Ultrafiltration of particle-free supernatants of crude and resin-treated whole cell broth.

| Supernatant Treatment (%, wt/v) | Average Transmembrane Flux Rate (liter/hr/$m^2$) |
| --- | --- |
| Control | 8.13 |
| Resin A (0.25%) + Resin B (0.10%) | 28.5 |

EXAMPLE 6

The procedure of Example 5 was repeated in all essential respects except that Resin A and then Resin B were added to cell-free supernatant at final concentrations of 0.25% and 0.10%, respectively. The improved performance of the ultrafiltration of the ion exchanger-treated, cell-free supernatant is shown in Table 6.

TABLE 6

Ultrafiltration of cell-free supernatant treated with mixed resins.

| Supernatant Treatment (%, wt/v) | Average Transmembrane Flux Rate (liter/hr/$m^2$) |
| --- | --- |
| Control (cell-free supernatant) | 8.13 |
| Resin A (0.25%) + Resin B (0.10%) | 22.8 |

EXAMPLE 7

Whole cells of Bacillus sp., ATCC 21536, were grown on a liquid medium containing 2% starch, 0.5% yeast extract, 0.5% peptone, 0.1% monopotassium phosphate, 0.02% magnesium sulfate and 1% sodium carbonate at 37° C. and pH 10.0 for three days. The final dry cell concentration, determined by precipitating the cells in a broth sample, washing the cell pellet, drying it at 80° C. for 30 hours and weighing it, was 4.6 g/liter. At the end of cultivation, one liter of crude fermentation broth was concentrated by ulrafiltration as described in Examples 1 and 3. The resins used and results are given in Table 7, and show that a substantial improvement (41%) in flux rate was obtained when Resin A was added to the fermentation medium. The flux was increased 59.3% by adding Resin B to the floc previously formed with Resin A.

TABLE 7

| Charged Particle Preparation (%, wt/v) | Average Transmembrane Flux Rate (liter/hr/$m^2$) | Average Protein Rejection |
| --- | --- | --- |
| None | 14.1 | 0.94 |
| Resin A (0.1%) | 19.9 | 0.93 |
| Resin A (0.1%) + Resin B (0.04%) | 31.7 | 0.85 |

EXAMPLE 8

The procedure of Example 7 was repeated example that the whole fermentation broth was concentrated by microfiltration at room temperature using a hollow fiber filtration module with a porosity of 0.1 μm (Romicon HF-1-47MP). This module has twenty-five fibers with an internal diameter of 1.1 mm, a surface area of 930 $cm^2$ and a length of 40 cm. The average permeate flux rate was measured and compared with those obtained when Resin A was added to the Bacillus sp. fermentation broth. The results of the measurements are given in Table 8, from which it may be seen that an improvement of 55% in flux rate was obtained over the control.

TABLE 8

| Resin A Concentration (%, wt/v) | Average Transmembrane Flux Rate (liter/hr/$m^2$) |
| --- | --- |
| None | 15.4 |
| 0.05 | 28.7 |
| 0.10 | 23.9 |

EXAMPLE 9

The procedure of Example 8 was repeated except that other microsized anion exchange resins were used for the concentration of a 4-day-old Bacillus broth. The average flux rates obtained during microfiltration are shown in Table 9 and indicate substantial improvements may be obtained by the addition of the microsized resins useful in the present invention.

TABLE 9

| Charged Particle Concentration (wt/v) (liter/hr/$m^2$) | Average Resin Diameter (μm) | Average Flux Rate |
| --- | --- | --- |
| None | | 14.2 |
| Resin A (0.10%) | 0.12 | 31.9 |
| Resin C (0.10%) | 0.22 | 32.7 |
| Resin D (0.18%) | 1.0 | 26.2 |

EXAMPLE 10

Whole yeast cells of *Saccharomyces cerevisiae* (5 g/liter) were suspended in 0.15 M sodium chloride at pH 7.0. Two 4-liter portions were treated with the resins useful in the present invention by first adding the amount of Resin A indicated in Table 10, and subsequently adding the indicated amount of Resin B. The treated portions and untreated suspension were concentrated by ultrafiltration as described in Example 1 and the results are given in Table 10. The resin additions increased the flux rates by 53% and 82%.

TABLE 10

| Charged Particle Preparation (% wt/v) | Average Flux Rate (liter/hr/$m^2$) |
|---|---|
| None | 38.4 |
| Resin A (0.001%) + Resin B (0.0004%) | 58.8 |
| Resin A 0.005%) + Resin B (0.002%) | 69.9 |

EXAMPLE 11

The procedure of Example 10 was repeated except that the yeast cell suspension was concentrated by microfiltration as described in Example 8. Table 11 shows the effect of Resin A and mixed Resins A and B on the average flux rates.

TABLE 11

| Charged Particle Preparation (% wt/v) | Average Flux Rate (liter/hr/$m^2$) |
|---|---|
| None | 35.0 |
| Resin A (0.005%) | 50.5 |
| Resin A (0.005%) + Resin B (0.002%) | 57.0 |

EXAMPLE 12

The procedure of Example 11 was repeated except that a 0.5 g/liter bovine serum albumen (BSA) solution was added to the yeast cell suspension and the protein rejection was measured. Table 12 shows the ability of mixed charge Resins A and B to improve flux and protein rejection.

TABLE 12

| Charged Particle Preparation (wt/v) | Average Flux Rate (liter/hr/$m^2$) | Average Protein Rejection |
|---|---|---|
| None | 45.5 | 0.75 |
| Resin A (0.001%) + Resin B (0.0004%) | 66.1 | 0.42 |

We claim:

1. An improved method for separating components of a liquid cell culture medium by membrane filtration which comprises:

(a) introducing into the medium an effective amount of a first charged, particulate material bearing 0.1–1.5 functional groups per monomer unit and having an average diameter of from about 0.01 to about 2.5 micrometers, to form a suspension in the medium, and (b) subjecting the medium containing the suspension to membrane filtration.

2. The method of claim 1 wherein, in step (a) subsequent to introduction of the first particulate material into the medium, an effective amount of a second charged particulate material bearing a charge opposite that of the first particulate material, bearing 0.1–1.5 functional groups per monomer unit and having an average diameter of from 0.01 to about 2.5 micrometers, is introduced into the medium.

3. The method of claim 2 wherein the first particulate material is an anion exchange resin and the second particulate material is a cation exchange resin.

4. The method of claim 3 wherein the anion exchange resin and the cation exchange resin have average particle diameters of about 1.5 micrometers or less.

5. The method of claim 2 wherein the first particulate material is strongly basic and the second particulate material is strongly acidic.

6. The method of claim 2 wherein the liquid cell culture medium comprises a fermentation broth.

7. The method of claim 6 wherein the fermentation broth is of a bacterium.

8. The method of claim 6 wherein the fermentation broth is of a yeast.

9. The method of claim 1 wherein the first particulate material is an anion exchange resin.

10. The method of claim 9 wherein the anion exchange resin has an average particle diameter of about 1.5 micrometers or less.

11. The method of claim 1 wherein the liquid cell culture medium comprises a fermentation broth.

12. The method of claim 11 wherein the fermentation broth is of a bacterium.

13. The method of claim 11 wherein the fermentation broth is of a yeast.

14. An improved method for separating components of a liquid cell culture medium by membrane filtration which comprises:

(a) introducing into the medium an effective amount of a first charged, particulate material bearing 0.1–1.5 functional groups per monomer unit and having an average diameter of from about 0.01 to about 2.5 micrometers, to form a suspension in the medium, (b) introducing into the medium an effective amount of a second charged particulate material bearing a charge opposite that of the first particulate material, bearing 0.1–1.5 functional groups per monomer unit and having an average diameter of from 0.01 to about 2.5 micrometers, (c) separating solid components from the medium, (d) resuspending said solid components in a second, aqueous, liquid medium, and (e) subjecting the second aqueous liquid medium to membrane filtration.

15. An improved method for separating components of a liquid cell culture medium by membrane filtration which comprises:

(a) introducing into the medium an effective amount of a first charged, particulate material bearing 0.1–1.5 functional groups per monomer unit and having an average diameter of from about 0.05 to about 2.5 micrometers, to form a suspension in the medium, (b) introducing into the medium an effective amount of a second charged particulate material bearing a charge opposite that of the first particulate material, bearing 0.1–1.5 functional groups per monomer unit and having an average diameter of from 0.01 to about 2.5 micrometers, (c) separating solid components from the medium, and (d) subjecting the medium to membrane filtration.

* * * * *